US012257407B2

(12) United States Patent
Yang et al.

(10) Patent No.: US 12,257,407 B2
(45) Date of Patent: Mar. 25, 2025

(54) INTRA-AORTIC DUAL BALLOON DRIVING PUMP CATHETER DEVICE

(71) Applicant: FUWAI HOSPITAL OF CHINESE ACADEMY OF MEDICAL SCIENCES, Beijing (CN)

(72) Inventors: Tao Yang, Beijing (CN); Yuejin Yang, Beijing (CN)

(73) Assignee: FUWAI HOSPITAL OF CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 18/454,077

(22) Filed: Aug. 23, 2023

(65) Prior Publication Data

US 2024/0066274 A1 Feb. 29, 2024

(30) Foreign Application Priority Data

Aug. 23, 2022 (CN) .......................... 202211012827.5

(51) Int. Cl.
*A61M 25/10* (2013.01)
*A61M 60/139* (2021.01)

(52) U.S. Cl.
CPC ...... *A61M 25/1011* (2013.01); *A61M 60/139* (2021.01); *A61M 2025/1013* (2013.01)

(58) Field of Classification Search
CPC ............ A61M 25/1011; A61M 60/139; A61M 2025/1013
See application file for complete search history.

(56) References Cited

U.S. PATENT DOCUMENTS

| | | | |
|---|---|---|---|
| 4,902,272 A | 2/1990 | Milder et al. | |
| 5,413,558 A | 5/1995 | Paradis | |
| 7,927,268 B1 | 4/2011 | St. Germain et al. | |
| 2010/0211008 A1 | 8/2010 | Wiest et al. | |
| 2018/0317932 A1 | 11/2018 | H'Doubler | |
| 2021/0138129 A1* | 5/2021 | Yang | A61M 60/139 |

FOREIGN PATENT DOCUMENTS

| | | |
|---|---|---|
| CN | 105816926 A | 8/2016 |
| CN | 110446523 A | 11/2019 |
| CN | 110876673 A | 3/2020 |
| CN | 215135916 U | 12/2021 |
| JP | 339172 A | 2/1991 |
| JP | 5212109 A | 8/1993 |
| WO | 2009035581 A1 | 3/2009 |
| WO | 2022126123 A1 | 6/2022 |

* cited by examiner

*Primary Examiner* — George R Evanisko
(74) *Attorney, Agent, or Firm* — Leydig, Voit & Mayer, Ltd.

(57) ABSTRACT

An intra-aortic dual balloon driving pump catheter device is disclosed, including a controlling part adapted to control air pumps to inflate and deflate a first balloon and a second balloon according to a cardiac cycle and an arterial pressure of the catheter end monitored by a monitoring part, such that in diastole the first balloon inflates while the second balloon deflates, and in systole the first balloon deflates while the second balloon inflates, wherein the second balloon deflates and inflates conversely to the synchronized inflation and deflation of the first balloon respectively, the first balloon fully inflates in diastole and fully deflates in systole, and the second balloon fully deflates in diastole and can inflate in systole only to a predetermined percentage of its volume of full inflation.

8 Claims, 3 Drawing Sheets

INTRA-AORTIC DUAL BALLOON DRIVING PUMP CATHETER DEVICE

FIELD

The present disclosure relates to an intra-aortic dual balloon driving pump catheter device in particular.

BACKGROUND

Intra-aortic balloon pump (IABP) is a mechanically assistive circulatory device widely and effectively used in the current clinical application. It is a cardiac catheterization therapy wherein a catheter with a balloon is placed through the arterial system to the proximal end of the descending thoracic aorta, or the end distal to the left subclavian artery opening, inflating and deflating of the balloon correspondingly to the cardiac cycle such that the blood flow changes in time phase within the aorta so as to mechanically assist the circulation. The aim is thus achieved to reduce aortic impendence and to increase cardiac output and aortic diastolic pressure while reducing myocardial oxygen consumption and increasing oxygen supply, so as to improve the function of the heart.

The intra-aortic balloon pump (IABP) may be applied to different situations to improve the patients' hemodynamics by increasing coronary artery perfusion and reducing afterload of ventricle. These factors improve the heart function and myocardial oxygen demand-supply ratio. Its role is quite mild, and generally the cardiac output does not increase by more than 20%. The indications of intra-aortic balloon pump (IABP) include treatment of acute myocardial ischemia with unstable hemodynamics, postoperative cardiogenic shock, advanced heart failure, transition before cardiac transplantation, assistance to low cardiac output syndrome during peri-intervention, peri-procedure, and post procedure of cardiac surgery of patients of high risk, and etc.

The intra-aortic balloon pump device comprises a balloon catheter, and a counterpulsation machine serving as a driving section of the balloon catheter. The balloon catheter consists of an air supply catheter and a cylindrical balloon secured to the catheter. The standard for selecting the balloon catheter is to block 90%-95% of the aortic lumen after the balloon is inflated, and the balloon volume is greater than 50% of the heart's stroke volume. The counterpulsation machine comprises a monitoring part, a controlling part, a vacuum pump, and an air compressor. The air supply catheter communicates the elongated cylindrical balloon with the vacuum pump and the air compressor. The monitoring part and the controlling part cooperates with each other to automatically identify the ECG or pressure signal according to the given parameters, automatically regulate the time phase of inflation and deflation, and automatically adjust the counterpulsation parameters so as to achieve the best counterpulsation effect, and automatically stop when there is a failure or abnormal stroke.

The balloon is inflated when the heart dilates, and the balloon is deflated when the heart contracts. The double effect of hemodynamics is thus produced. On one hand, the balloon is inflated in the diastole, so as to occupy the space of the blood. In this case, as the aortic valve has closed, so that the inflated balloon quickly drives blood to both the distal and the proximal sides of the aorta, whereby driving blood to the distal (cordis) side of the balloon increases the diastolic pressure at the aortic root, and thus increases the coronary and cerebral artery blood supply for heart and brain; and driving blood to the proximal (peripheral) side of the balloon increases the peripheral perfusion of whole body, and thus increases the diastolic peripheral pressure and support the cardiac circulation. On the other hand, the balloon is deflated during the systole, so as to produce the aortic negative pressure instantly to greatly lowers the work load of the left ventricle (cardiac afterload), Thus the cardiac output is increased and the myocardial oxygen consumption reduced, improving the left ventricular ejection and circulatory blood supply.

The counterpulsation of the balloon is usually triggered by the arterial waveform recorded at the top of the balloon, or is controlled by the electrocardiographic QRS waveform with time. The balloon counterpulsation must be inflated and deflated at very early time points in both diastole and systole of each cardiac cycle respectively. Ideally, the balloon shall be inflated in diastole when the aortic valve is just closed, corresponding to the end of electrocardiographic T wave or the early descending waves of arterial waveform. Meanwhile, it is preferable that the balloon is deflated in systole just before the aortic valve opening, i.e. about to eject of the left ventricle, corresponding to the electrocardiographic QRS wave or the end of descending waves of arterial waveform. Premature deflation in systole may bring poor efficacy.

The current clinical IABP catheter can be only inflated and deflated by its balloon corresponding to the cardiac cycle to cause mild increase in the blood pumped within the aorta, but cannot control the blood to move one-way ahead, or actively drive the blood.

Japanese patent application dated Aug. 24, 1993, entitled "Balloon Pumping System," with Publication No. H05212109, discloses a balloon pumping system in which both balloons inflate in diastole and deflate one after the other in systole, in which the valve balloon deflates a little later (a few milliseconds). In diastole, the balloons inflate through a one-way valve such that the large pumping balloon and the small valve balloon inflate simultaneously, while in systole, they deflate through the one-way valve such that the large pumping balloon deflates first, followed by the deflation of the small valve balloon.

U.S. Patent U.S. Pat. No. 4,902,272, filed on Jun. 17, 1987, entitled "Intra-arterial Cardiac Support System," discloses an intra-arterial cardiac support system comprising a first balloon and a second balloon arranged in a longitudinal direction of the catheter in front and behind the catheter respectively, wherein the first balloon is a pumping balloon located at the distal end of the catheter and the second balloon is a valve balloon located closer to the proximal end of the catheter than the first balloon. When the diastolic phase of the heart begins and the first balloon inflates, the second balloon is already in an inflated state and has not begun to deflate; when the second balloon begins to deflate, the first balloon remains inflated and is not in a deflated state, and therefore does not begin to inflate at the same time; when the second balloon begins to inflate, and the first balloon remains inflated and does not begin to deflate. The same is true during systole of the heart. Thus, there is no such a situation that the first and second balloons are simultaneously and oppositely inflating one and deflating the other.

In the present applicant's Chinese granted patent CN110876673B dated Nov. 8, 2019, entitled "intra-aortic dual balloon driving pump catheter device," an intra-aortic dual balloon driving pump catheter device is disclosed, in which a first "pump" balloon located at the distal end of the catheter and a second "valve" balloon located at the proximal end of the catheter are arranged successively along the longitudinal direction of the catheter, wherein the second balloon deflates and inflates conversely to the synchronized inflation and deflation of the first balloon respectively, wherein in diastole the first balloon inflates while the second balloon deflates, and in systole the first balloon deflates while the second balloon inflates.

However, clinically there is not only a need to provide an intra-aortic balloon driving pump catheter capable of driving blood forward in a unidirectional manner, but also a desire to be able to modulate the administration of varying intensities of circulatory support in response to varying clinical circulatory failure needs, which is not at all contemplated in the current prior art.

SUMMARY

Said technical problem may be solved by the present invention providing an intra-aortic dual balloon driving pump catheter device. The intra-aortic dual balloon driving pump catheter device comprises: a catheter; a first balloon and a second balloon, the first balloon and the second balloon surrounding the catheter, being arranged successively along the longitudinal direction of the catheter, wherein the first balloon is a counterpulsation balloon, being placed at the distal end of catheter, and the second balloon is a valve balloon, being placed immediately adjacent to the proximal end of the first balloon and is closer to the proximal end of the catheter than the first balloon; a monitoring part, for monitoring the cardiac cycle and the arterial pressure of the catheter end; air pumps, respectively associated with the first balloon and the second balloon for supplying and withdrawing air; a first intake pipe and a second intake pipe, one end of which is in communication with the first balloon and the second balloon respectively, and the other end of which is in communication with the respectively associated air pump; a controlling part, adapted to control the air pumps to inflate and deflate the first balloon and the second balloon according to the cardiac cycle and the arterial pressure of the catheter end monitored by the monitoring part, such that in diastole the first balloon inflates while the second balloon deflates, and in systole the first balloon deflates while the second balloon inflates, wherein the second balloon deflates and inflates conversely to the synchronized inflation and deflation of the first balloon, wherein the first balloon fully inflates in diastole and fully deflates in systole, and the second balloon can be completely deflated when deflating (in diastole) and can inflate (in systole) only to a predetermined percentage of its volume of full inflation.

Therefore, the present invention has proposed an adjustable intra-aortic dual balloon driving pump catheter in which the degree of inflation of the second balloon can be adjusted.

In diastole, the first balloon inflates and the second balloon deflates, which brings the following effects: the inflation of the first balloon per se drives the blood to both the proximal (cordis) and the distal (peripheral) sides of the aorta, so that the diastolic pressure at the aortic root is increased, thereby increasing both of the coronary and cerebral artery blood supply for myocardium and brain, and also promoting peripherally the blood supply and perfusion to the whole body.

In systole, the first balloon deflates and the second balloon inflates, which brings the following blood-driving effects: deflating the first balloon causes rapidly blood space emptying and pressure decreasing in the aorta, and then blood sucked into the aorta from the ejecting heart, which remarkably pumps upstream heart blood into the aorta due to the maximal pressure difference between the ejecting heart and the emptied aorta generated by the combination of the first balloon deflating and the second balloon blocking to stop blood reflux from distal aorta, and thus drives the blood forward downstream ahead in diastole of the next cardiac cycle. As a result, the blood circulation will be not only intensified, pushed and driven, but also kept in the unidirectional forward ahead, which can actively and strongly support the normal circulation state for circulatory failure or even collapse.

Herein, although the deflation and inflation of the first and second balloons also act simultaneously just like in cardiac diastole, the inflation of the second balloon in systole can only reach a predetermined percentage of the volume at full fill under the control of the controlling part, such as 100% or 75% or 50% or 25% or 0%. The second balloon acts as a valve balloon, and its complete filling implies an optimal inflation blockage and circulatory support effect, which both enhances the suction-pumping effect provided by the deflation of the first counterpulsation balloon and ensures that the forward blood flow cannot be pumped back. However, it is necessary to set the inflation volume of the second (valve) balloon to only a predetermined percentage of its volume of full inflation if considering the different degrees of circulatory support required for different degrees of circulatory failure of the patients (further, the percentage of the volume of the inflated second (valve) balloon in relation to its volume of full inflation may be set to a number of adjustable level options), thereby allowing forward blood flow in distal (peripheral) aorta to be refluxed back when the first balloon deflates in systole to meet the needs of patients with varying degrees of circulatory failure, as well as the transitional needs of patients with improved circulatory function before fully recovered or deactivation. This allows for more precise and appropriate circulatory support for patients with different degrees of circulatory failure.

The first balloon and the second balloon are in communication with the respectively associated air pump via a first intake pipe and a second intake pipe. There may be multiple embodiments for the arrangement of the intake pipes and the catheter.

According to an embodiment of the intra-aortic dual balloon driving pump catheter device according to the present invention, the first intake pipe surrounds the catheter and extends together therewith through the second balloon. Preferably, after extending through the second balloon, the first intake pipe and the catheter surrounded by the first intake pipe extend in parallel with the second intake pipe. Or, in another preferable embodiment, after extending through the second balloon, the first intake pipe is surrounded by and extends together with the second intake pipe.

According to another embodiment of the intra-aortic dual balloon driving pump catheter device according to the present invention, after extending through the second balloon respectively, the catheter and the first intake pipe extend in parallel with the second intake pipe.

According to an embodiment of the intra-aortic dual balloon driving pump catheter device according to the present invention, the first balloon has a length longer than that of the second balloon. The first balloon and the second balloon play different roles in the process of successive actions. The first balloon is mainly to work as a counterpulsation balloon for blood pump, while the second balloon to a valve balloon to stop blood reflux when the first balloon deflation for the blood to move downstream forward. The volume expanded by inflation of the first balloon determines the effects of sucking the upstream heart blood into aorta and driving the aorta blood to move downstream ahead. A shorter second balloon helps to stop blood reflux as a "valve" during the first balloon deflation and to promote more blood downstream when it is deflated.

Preferably, the first balloon has a length that is nine-tenth of a total length of the first balloon and the second balloon.

According to a preferable embodiment of the intra-aortic dual balloon driving pump catheter device according to the present invention, the second balloon first fully inflates after the intra-aortic dual balloon driving pump catheter device is set in the aortic, and the controlling part then adjusts the percentage of the volume of the inflated second balloon in relation to its volume of full inflation. This can be set based on an assessment of the supportive effect on circulatory failure suggested by clinical feedback, or be adjusted at any time to a percentage of the volume of the inflated second balloon in relation to its volume of full inflation based on the supportive effect on circulatory failure suggested by clinical hemodynamic (arterial blood pressure and peripheral tissue perfusion) feedback.

Preferably, the controlling part sets the percentage level options of the volume of the inflated second balloon in relation to its volume of full inflation based on the arterial pressure monitored by the monitoring part and the supportive effect on circulatory failure suggested by clinical feedback.

It should be understood that once the percentage of the volume of the inflated second balloon in relation to its volume of full inflation has been adjusted and set, it should be maintained and should not be adjusted arbitrarily again for a certain period of time in principle, in order to ensure the stability of the hemodynamic state of the patient with circulatory failure and the stability of the circulatory supportive effect. A number of preset values (e.g., 100%, 75%, 50%, 25%, and 0%), for the percentage of the volume of the inflated second balloon in relation to its volume of full inflation, may be stored in the controlling part as value options for clinical selection, so as to achieve a fast, stable, and repeatable adjustment effect. The intra-aortic dual balloon driving pump catheter device as a whole, its catheter, balloons, and intake pipes must be disposable in accordance with medical and health requirements; while the air pumps, monitoring part, and controlling part connected to the intra-aortic dual balloon driving pump catheter device are identical to those of the traditional intra-aortic balloon driving pump (IABP) instrument, and together they are presented as a bedside removable whole machine.

Thus, advantageously, a number of discrete numerical points (corresponding to a number of operation level options) are preset in the controlling part as options for values to be taken when the percentage of the volume of the inflated second balloon in relation to its volume of full inflation being adjusted. The interval steps between each of the discrete numerical points are identical, in order to facilitate easy and fast standardized operation in the case of first aid to the patient.

Preferably, it is possible to set five level options for clinical selection, by which the volume of the inflated second balloon can reach 100% or 75% or 50% or 25% or even 0% of its volume of full inflation. It is also possible to set the percentage of the volume at which the second balloon reaches in relation to its volume of full inflation as five level options including 100% or 85% or 65% or 35% or 0% for selection. It should be understood, however, that the 100% level option is the intra-aortic dual balloon driving pump mode while the 0% level option is the conventional simple IABP mode, that is, as an adjustable intra-aortic dual balloon driving pump catheter, by setting the degree of inflation of the second balloon to its boundary values, it is also possible to realize the function of a simple intra-aortic balloon pump catheter (IABP) in the prior art and an intra-aortic dual balloon driving pump catheter (IADBP) proposed by the present applicant's authorized patent CN110876673B in China, which provides an easy-to-operate option for clinical patients' needs. Obviously, it is also possible not to set 100% as a predetermined value of a volume percentage of the inflated second balloon in relation to its volume of full inflation. In this case, the present invention will simply provide an adjustable intra-aortic dual balloon driving pump catheter, in which case it can't be equivalent to the intra-aortic dual balloon driving pump catheter (IADBP) proposed by the present applicant in the granted Chinese patent CN110876673B, as the second balloon's volume will not reach 100% of the volume of full inflation.

It is also possible to preset the percentage of the volume of the inflated second balloon in relation to its volume of full inflation as a continuous range of values, and then slightly adjust by increasing or decreasing the degree of inflation of the second balloon during each cardiac cycle in multiples of a certain interval step (e.g., in 5% or multiples of 5%), i.e., the percentage of the volume of the inflated second balloon in relation to its volume of full inflation, based on the supportive effect on circulatory failure suggested by clinical feedback.

DETAILED DESCRIPTION

The intra-aortic dual balloon driving pump catheter device of the present invention will be described in detailed embodiments with reference to the accompanying drawings. It shall be noted that the accompanying drawings are given by way of illustration only, and shall not be construed as limiting the present invention.

The intra-aortic dual balloon driving pump catheter device is guided by a guide wire 1 of a catheter 2 and reaches a predetermined position within the aorta, and then the guide wire 1 exits from the catheter 2.

Figure 1:
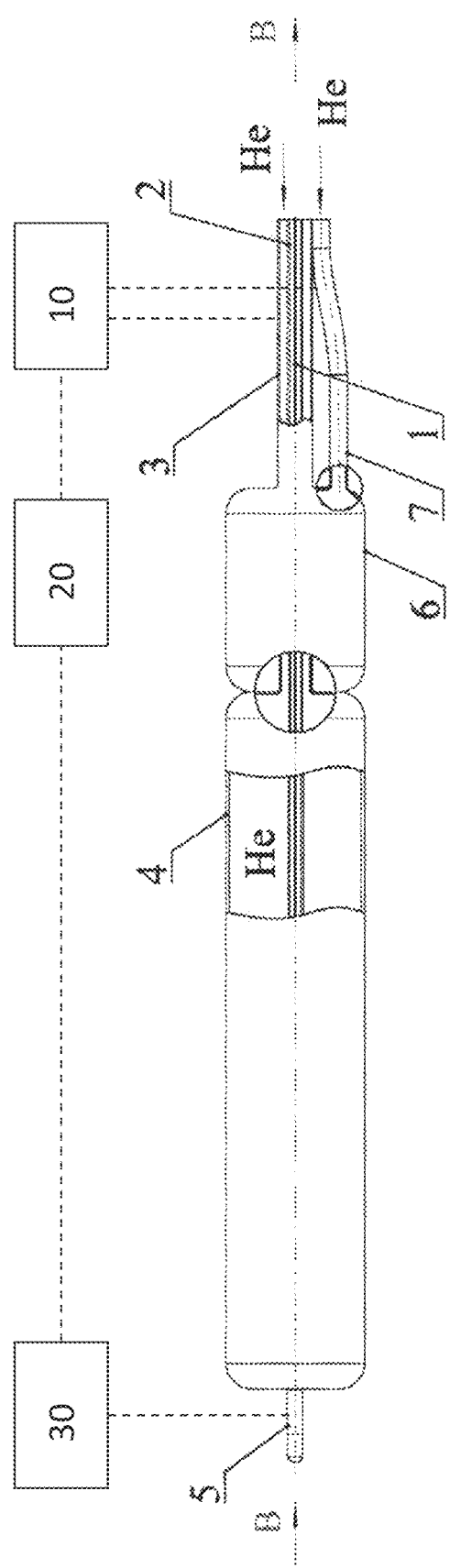
FIG. 1 shows a partial section view of an intra-aortic dual balloon driving pump catheter device according to a first embodiment of the present invention.

FIG. 1 shows a partial section view of an intra-aortic dual balloon driving pump catheter device according to the first embodiment of the present invention. As shown in the figure, a first balloon 4 and a second balloon 6 are arranged to successively surrounding the catheter 2 along the longitudinal direction of the catheter 2, wherein the position of the first balloon 4 is closer to a distal end of catheter 5 than the position of the second balloon 6. A first intake pipe 3 and a second intake pipe 7 have one end in communication with the first balloon 4 and the second balloon 6 respectively, and the other end in communication with the air pump 10 respectively associated with the balloons and used for supply and withdrawal of air.

Figure 2:
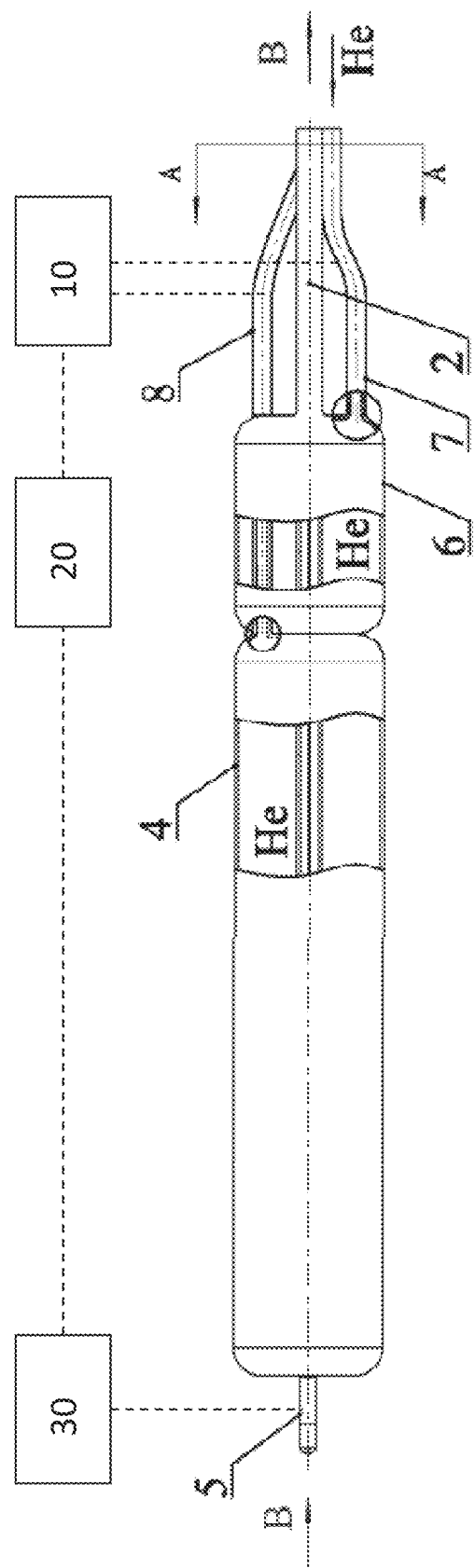
FIG. 2 shows a partial section view of an intra-aortic dual balloon driving pump catheter device according to a second embodiment of the present invention.
Figure 3:
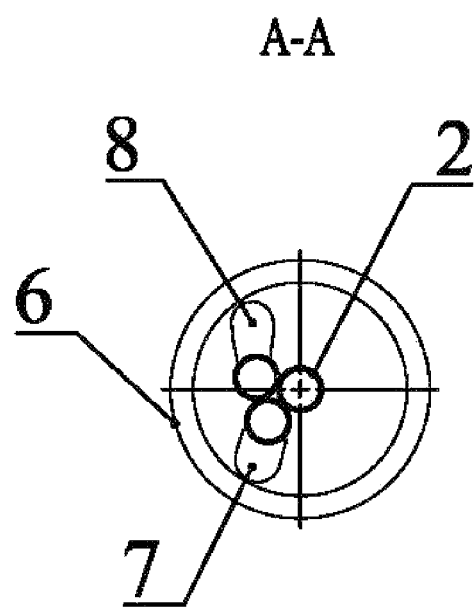
FIG. 3 shows a cross section view of an intra-aortic dual balloon driving pump catheter device according to the second embodiment of the present invention.

FIG. 2 shows a partial section view of an intra-aortic dual balloon driving pump catheter device according to the second embodiment of the present invention. It differs from the first embodiment of the present invention in that, the first intake pipe 8 protruding from the first balloon 4 does not surround the catheter 2 which is through the first balloon 4 and the second balloon 6, but passes through the second balloon 6 individually. The first intake pipe 3 through the second balloon 6, the catheter 2, and the second intake pipe 7 protruding from the second balloon 6 extend in parallel with each other as shown in the figure.

The intra-aortic dual balloon driving pump catheter device of the present invention further comprises a monitoring part 30 and a controlling part 20. The monitoring part 30 is used for monitoring the cardiac cycle and the arterial pressure of the catheter end 5, while the controlling part 20 is adapted to control the air pumps 10 to inflate and deflate the first balloon 4 and the second balloon 6 according to the cardiac cycle and the arterial pressure of the catheter end 5 monitored by the monitoring part, such that the first balloon 4 periodically inflates in diastole to occupy the space of blood in aorta, so as to push blood towards both sides of the first balloon, whereas deflates in systole to create space, so as to proactively extract pumped-out blood from the heart, and thus increases the cardiac output; and the second balloon inflates in systole to block the distal end of the aorta to prevent the blood flow at the distal end of the aorta from returning when the first balloon deflates, and deflates in diastole to make the blood flow created by the inflation of the first balloon be pushed forward downstream.

In this embodiment, the first intake pipe 8 protruding from the first balloon 4 surrounds and extends together with the catheter 2 through the second balloon 6, and then extends in parallel with the second intake pipe 7 protruding from the second balloon 6. An air pump associated with the first intake pipe 8 and the second intake pipe 7 respectively may supply, for example, helium gas into the first balloon 4 and the second balloon 6 to inflate the latter. The whole process of inflation is required to be completed within 130 ms. However, the air pumps are controlled such that the first balloon 4 inflates in diastole and deflates in systole, while the second balloon 6 inflates in systole and deflates in diastole. In diastole, the inflation of the first balloon 4 synchronizes with the deflation of the second balloon 6; in systole, the deflation of the first balloon 4 synchronizes with the inflation of the first balloon 6.

In diastole, the inflation of the first balloon 4 per se drives the blood to both the distal (cordis) and the proximal (peripheral) sides of the balloon in aorta, so that the diastolic pressure at the aortic root and coronary artery blood and myocardial oxygen supply are increased, and the blood is also simultaneously pushed forward downstream to supply the whole body. The second balloon deflates in diastole to make the blood flow created by the inflation of the first balloon be pushed forward downstream.

In systole, the negative pressure generated by the deflation of the first balloon 4 draws blood into the aortic cavity created by deflation, resulting in a decrease in the ejection resistance of the heart, or a decrease in the afterload of the heart, and an increase in the volume of blood expelled from the heart. The inflation of the second balloon 6 takes place at the same time when the first balloon 4 is deflating, thus the second balloon 6 forms a valve blocking the blood from being refluxed back into the cavity, such that the pumping effect caused by the deflation of the first balloon 4 does not affect the advancing blood downstream from the second balloon 6.

Herein, the air pumps are controlled such that the inflation and the deflation of the first balloon 4 synchronizes with the deflation and the inflation of the second balloon. That is, in diastole the first balloon 4 inflates while the second balloon 6 deflates, and in systole the first balloon 4 deflates while the second balloon 6 inflates, wherein the second balloon 6 deflates and inflates conversely to the synchronized inflation and deflation of the first balloon 4. Herein, the first balloon 4 fully inflates in diastole and fully deflates in systole, and the second balloon 6 fully deflates in diastole and can inflate in systole only to a predetermined percentage of its volume of full inflation. The predetermined percentage can be 100%, or 0%, or any intermediate value between 0% and 100%.

After the intra-aortic dual balloon driving pump catheter device is set in the aortic, the controlling part sets a percentage of the volume of the inflated second balloon 6 in relation to its volume of full inflation, which is based on an assessment of the supportive effect on circulatory failure suggested by clinical feedback. During the pumping process of the intra-aortic dual balloon driving pump catheter device within the aorta, the second balloon 6 always inflates to the same degree defined by this predetermined percentage. Thereafter, the controlling part can also adjust the percentage of the volume of the inflated second balloon 6 in relation to its volume of full inflation based on the supportive effect on circulatory failure suggested by clinical feedback. Typically, the percentage of the volume of the inflated second balloon 6 in relation to its volume of full inflation should be maintained at 100%, i.e. IADBP mode, by default, which can be adjusted based on the state of circulatory failure and the effect of circulatory support after the intra-aortic dual balloon driving pump catheter device has been placed (set in the aortic). Adjustments can be made easily and quickly by commands from the controlling part.

In particular, a number of discrete numerical points or a continuous range of numerical values are preset in the controlling part as the range of values to be taken for the percentage of the volume of the inflated second balloon in relation to its volume of full inflation, which makes it easy to qualitatively (i.e., to divide into different level options defined by the preset discrete value points) or quantitatively adjust the degree of inflation of the second balloon based on the state of circulatory failure and the effect of the circulatory support in the case of clinical use. For example, preset 0% or 25% or 50% or 75% or 100% as a set of possible ranges of values to be taken for the percentage of the volume of the inflated second balloon 6 in relation to its volume of full inflation, or preset 0% or 35% or 65% or 85% or 100% as a set of possible ranges of values to be taken. The interval steps between the discrete numerical points (level options) of the above first set of preset values are all evenly 25%. It should be understood that it is more advantageous to set the interval steps between these preset discrete numerical points (level options) to be equal, as it is clear that equal interval step settings facilitates easy and accurate clinical operation.

If a number of continuous ranges of numerical values is preset in the controlling part as the range of values to be taken for the percentage of the volume of the inflated second balloon in relation to its volume of full inflation, it would be possible to temporarily adjust the percentage of the volume of the inflated second balloon in relation to its volume of full inflation, by a preset interval step or its multiples, based on the state of circulatory failure and the effect of circulatory support. For example, first set it as 100% by default, and then select a certain volume percentage X % in a continuous range of numerical values from 100% to 30%, and if further adjustment is required, that volume percentage is adjusted in interval steps of 5% or multiples of 5%. This type of quantitative adjustment in predetermined interval steps helps the clinical user to quickly establish a feedback experience between the quantity of adjustment and the effect of the adjustment.

While the present invention has been described with reference to the preferred embodiments, the spirit and scope of the invention are not limited to the disclosure herein. According to the teaching of the present invention, those skilled in the art are able to deduce more embodiments and applications without departing from the spirit and scope of the present invention, which are not defined by the embodiments but by the appended claims.

The invention claimed is:

1. An intra-aortic dual balloon driving pump catheter device, comprising:
   a catheter;
   a first balloon and a second balloon, respectively surrounding the catheter, being arranged successively along a longitudinal direction of the catheter, wherein the first balloon is a counterpulsation balloon, being placed at a distal end of the catheter, and the second balloon is a valve balloon, being placed adjacent to a proximal end of the first balloon and is closer to a proximal end of the catheter than the first balloon;
   monitor, for monitoring a cardiac cycle and an arterial pressure of the distal end;
   air pumps, respectively associated with the first balloon and the second balloon, for supplying and withdrawing air;
   a first intake pipe having a first end and a second end, the first end of the first intake pipe being in communication with the first balloon, and the second end of the first intake pipe being in communication with the air pump associated with the first balloon;
   a second intake pipe having a first end and a second end, the first end of the second intake pipe being in communication with the second balloon and the second end of the second intake pipe being in communication with the air pump associated with the second balloon;
   a controller, adapted to control the air pumps to inflate and deflate the first balloon and the second balloon according to the cardiac cycle and the arterial pressure of the distal end monitored by the monitor, wherein in diastole the first balloon inflates while the second balloon deflates, and in systole the first balloon deflates while the second balloon inflates or does not inflate,
   wherein the controller includes a first mode, wherein, in the first mode, the second balloon deflates and inflates conversely to the synchronized inflation and deflation of the first balloon respectively, the first balloon fully inflates in diastole and fully deflates in systole, and the second balloon fully deflates in diastole and inflates in systole only to a predetermined percentage of its volume of full inflation,
   wherein the catheter is configured to be placed in the aorta, and, when the catheter is placed in the aorta, the controller adjusts the percentage of the volume of the inflated second balloon in relation to its volume of full inflation based on the arterial pressure of the distal end, wherein the arterial pressure corresponds to a supportive effect on circulatory failure,
   wherein a number of discrete numerical points are preset in the controller as options for values to be taken when adjusting the percentage of the volume of the inflated second balloon in relation to its volume of full inflation,
   wherein the controller further includes identical interval steps between each adjacent pair of the discrete numerical points in order to adjust the percentage with the interval steps.

2. The intra-aortic dual balloon driving pump catheter device according to claim 1, wherein the controller sets the predetermined percentage of the volume of the inflated second balloon in relation to its volume of full inflation based on the arterial pressure monitored by the monitor.

3. The intra-aortic dual balloon driving pump catheter device according to claim 1, wherein each interval step is at least 5% of the volume of full inflation of the second balloon.

4. The intra-aortic dual balloon driving pump catheter device according to claim 1, wherein in the first mode when the second balloon fully deflates in diastole and inflates in systole only to the predetermined percentage of its volume of full inflation, the volume of the inflated second balloon is set to one of 100%, 75%, 50%, or 25% of its volume of full inflation,
   wherein the controller further includes a second mode,
   wherein in the second mode, the second balloon fully deflates in diastole and does not inflate in systole, and the volume of the inflatable second balloon is set to 0% of the volume of full inflation of the second balloon.

5. The intra-aortic dual balloon driving pump catheter device according to claim 1, wherein the controller further includes the first mode and a second mode,
   wherein in the first mode, the second balloon fully deflates in diastole and inflates in systole only to the predetermined percentage of its volume of full inflation, the volume of the inflated second balloon is set to one of 100%, 85%, 65%, or 35% of its volume of full inflation,
   wherein in the second mode, the second balloon fully deflates in diastole and does not inflate in systole, the volume of the inflatable second balloon is set to 0% of the volume of full inflation of the second balloon.

6. The intra-aortic dual balloon driving pump catheter device according to claim 1, wherein a plurality of numerical values from a continuous range are predetermined in the controller as candidate values to be taken when adjusting the percentage of the volume of the inflated second balloon in relation to its volume of full inflation.

7. The intra-aortic dual balloon driving pump catheter device according to claim 6, wherein, after setting the percentage of the volume of the inflated second balloon in relation to its volume of full inflation based on the plurality of predetermined numerical values in the continuous range, an adjustment of the percentage of the volume of the inflated second balloon in relation to its volume of full inflation is carried out in multiples of a certain interval step.

8. The intra-aortic dual balloon driving pump catheter device according to claim 7, wherein the interval step is at least 5% of the volume of full inflation of the second balloon.

* * * * *